United States Patent
Asaka et al.

(10) Patent No.: US 6,169,168 B1
(45) Date of Patent: Jan. 2, 2001

(54) ERYTHROMYCIN A DERIVATIVES

(75) Inventors: Toshifumi Asaka; Masato Kashimura; Tomohiro Sugimoto; Tetsuya Tanikawa; Takaaki Ishii; Akiko Matsuura, all of Tokyo (JP)

(73) Assignee: Taisho Pharmaceuticals Co., Ltd., Tokyo (JP)

( * ) Notice: Under 35 U.S.C. 154(b), the term of this patent shall be extended for 0 days.

(21) Appl. No.: 09/403,877

(22) PCT Filed: Oct. 22, 1998

(86) PCT No.: PCT/JP98/04780

§ 371 Date: Oct. 28, 1999

§ 102(e) Date: Oct. 28, 1999

(87) PCT Pub. No.: WO99/21868

PCT Pub. Date: May 6, 1999

(30) Foreign Application Priority Data

Oct. 29, 1997 (JP) .................................................. 9-296823

(51) Int. Cl.$^7$ .................................................. C07H 17/08
(52) U.S. Cl. .............................................. 536/7.4; 536/7.2
(58) Field of Search ......................... 536/7.2, 7.5; 514/29

(56) References Cited

U.S. PATENT DOCUMENTS

| | | | |
|---|---|---|---|
| 4,331,803 | 5/1982 | Watanabe et al. | 536/7.2 |
| 4,742,049 | 5/1988 | Baker et al. | 514/29 |
| 5,770,579 | 6/1998 | Agouridas et al. | 514/29 |

FOREIGN PATENT DOCUMENTS

| | | |
|---|---|---|
| 0 487 411 A1 | 5/1992 | (EP) . |
| 0 619 320 A1 | 10/1994 | (EP) . |

OTHER PUBLICATIONS

Hunt et al. The Journal of Antibiotics, vol. 42, No. 2, pp. 293–298, Feb. 1989. See PCT search report.

Primary Examiner—Elli Peselev

(74) Attorney, Agent, or Firm—Armstrong, Westerman, Hattori, McLelland & Naughton

(57) ABSTRACT

An erythromycin A derivative represented by the formula:

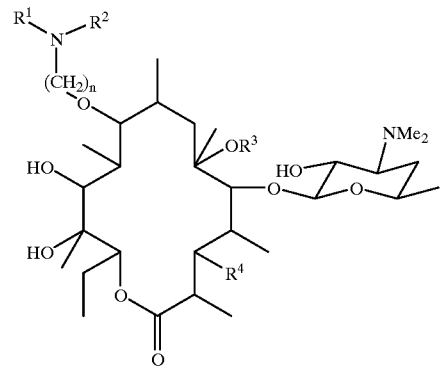

wherein n is an integer of from 1 to 8, $R^1$ is a hydrogen atom or an alkyl group having 1 to 6 carbon atoms, $R^2$ is a pyridylmethyl group, a quinolylmethyl group, a pyridylsulfonyl group or quinolylsulfonyl group, $R^3$ is a hydrogen atom, an alkyl group having 1 to 6 carbon atoms or a cinnamyl group, $R^4$ is a cladinosyloxy group or a group represented by the formula:

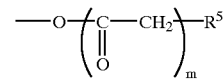

wherein m is 0 or 1, $R_5$ is a pyridyl group, a quinolyl group, a phenyl group, a phenyl group substituted with one, two or three members selected from alkyl groups having 1 to 6 carbon atoms, a nitro group, alkoxy groups having 1 to 3 carbon atoms and halogen atoms, or a pyridyl or quinolyl group substituted with one or two members selected from alkyl groups having 1 to 6 carbon atoms, a nitro group, alkoxy groups having 1 to 3 carbon atoms and halogen atoms; or a pharmaceutically acceptable salt thereof.

1 Claim, No Drawings

ERYTHROMYCIN A DERIVATIVES

This application is a 371 of PCT/JP98/04780, filed Oct. 22, 1988.

TECHNICAL FIELD

The present invention relates to novel derivatives of antibiotic erythromycin A.

BACKGROUND ART

Erythromycin A is an antibiotic widely used as an agent for the treatment of infectious diseases caused by Gram-positive bacteria, mycoplasmas, etc. However, erythromycin A is decomposed by gastric acid due to its instability to acids, and thus has a drawback of no constancy of movement in the body. Hitherto many erythromycin derivatives have been prepared for the purpose of the improvement of such biological or pharmaceutically effective properties. For example, it is reported that 6-O-methylerythromycin A derivatives have an improved stability to acids and have a superior in vivo antibacterial activity in comparison with erythromycin A when administered orally (U.S. Pat. No. 4,331,803). There are also recent reports relating to 11,12-cyclic carbamate derivatives obtained from 6-O-methylerythromycin A as a starting material with the aim of expansion of antibacterial spectrum as well as a stability to acids (EP. Patent No. 487411, U.S. Pat. No. 4,742,049). In addition, the present inventors have reported the antibacterial activity of the ester derivatives esterified at the 3-position (EP. Patent No. 619320).

An object of the present invention is to provide post-generational macrolide antibiotics having a strong antibacterial activity not only against previous erythromycin-sensitive bacteria but also against erythromycin-resistant bacteria which recently show a tendency to increase.

DISCLOSURE OF THE INVENTION

The present inventors have found that the compounds wherein a certain substituted aminoalkyl group or a certain alkyl group having an arylsulfonamide group has been introduced into the hydroxyl group formed by the reduction of the carbonyl group at the 9-position of erythromycin A have a strong antibacterial activity not only against sensitive bacteria but also resistant bacteria, thereby the present invention has been accomplished.

The present invention relates to an erythromycin A derivative represented by the formula:

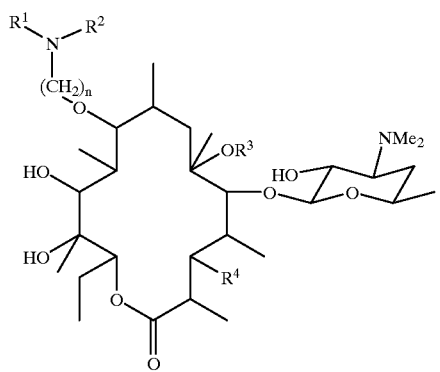

wherein n is an integer of from 1 to 8, $R^1$ is a hydrogen atom or an alkyl group having 1 to 6 carbon atoms, $R^2$ is a pyridylmethyl group, a quinolylmethyl group, a pyridylsulfonyl group or a quinolylsulfonyl group, $R^3$ is a hydrogen atom, an alkyl group having 1 to 6 carbon atoms or a cinnamyl group, $R^4$ is a cladinosyloxy group or a group represented by the formula:

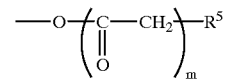

wherein m is 0 or 1, $R^5$ is a pyridyl group, a quinolyl group, a phenyl group, a phenyl group substituted with one, two or three members selected from alkyl groups having 1 to 6 carbon atoms, a nitro group, alkoxy groups having 1 to 3 carbon atoms and halogen atoms, or a pyridyl or quinolyl group substituted with one or two members selected from alkyl groups having 1 to 6 carbon atoms, a nitro group, alkoxy groups having 1 to 3 carbon atoms and halogen atoms; or a pharmaceutically acceptable salt thereof.

In the present invention, examples of the alkyl group having 1 to 6 carbon atoms are a methyl group, an ethyl group, a propyl group, a butyl group, a pentyl group, a hexyl group, an isopropyl group, an isobutyl group, a t-butyl group, an isopentyl group and a cyclohexyl group; examples of the alkoxy group having 1 to 3 carbon atoms are a methoxy group, an ethoxy group, a propoxy group and an isopropoxy group; and the halogen atom refers to a fluorine atom, a chlorine atom, a bromine atom or an iodine atom.

The pharmaceutically acceptable salt refers to a salt used in chemotherapy or prophylaxis of bacterially infectious diseases. It includes, for example, a salt with an acid such as acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, p-toluenesulfonic acid, laurylsulfuric acid, malic acid, aspartic acid, glutaminic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, polyacrylate or carboxyvinyl polymer.

The compounds of the present invention can be prepared according to the bellow-mentioned examples.

The erythromycin A derivatives of the present invention can be administered orally or parenterally. They can be administered in a dosage form such as tablets, capsules, powders, troches, ointments, suspensions, suppositories or injectional preparations, all of which can be prepared by ordinary preparation techniques. The dose is from 100 to 1,000 mg per day for the treatment of adults, and it can be administered once or in several divided portions. This dose can be properly increased or decreased depending on the age, body weight and conditions of the patient.

BEST MODE FOR CARRYING OUT THE INVENTION

The present invention is illustrated in more detail by the following examples and experiment.

EXAMPLE 1

9-Deoxo-9-hydroxy-9-O-[2-[N-methyl-N-(3-pyridylmethyl)amino]ethyl]erythromycin A (1) In 100 ml of tetrahydrofuran was dissolved 2.2 g (3.0 mmol) of 2'-O-acetyl-9-deoxo-9-hydroxyerythromycin A synthesized by the method described in the literature (J. Org. Chem., 47, 5019 (1982)), and then 1.8 g (8.8 mmol) of 2-bromoethylamine hydrochloride and 1.6 g (28.5 mmol) of potassium hydroxide were added, followed by stirring overnight. The reaction solution was diluted with ethyl acetate, washed with water and a saturated aqueous sodium chloride solution successively, and dried over anhydrous magnesium sulfate. The solvent was evaporated under reduced pressure, and the resulting residue was purified by silica gel column chromatography (chloroform:methanol:aqueous ammonia= 20:1:0.1) to give 0.8 g (yield: 34%) of 2'-O-acetyl-9-deoxo-9-hydroxy-9-O-(2-aminoethyl)erythromycin A.

(2) In 10 ml of methylene chloride was dissolved 1.3 g (1.6 mmol) of the compound obtained in the above (1), and then 0.18 g (1.7 mmol) of nicotinaldehyde and 0.64 g (3.0 mmol) of sodium triacetoxyborohydride were added, followed by stirring for an hour. Then, 0.25 ml (3.0 mmol) of 37% aqueous formaldehyde solution and 0.32 g (1.5 mmol) of sodium triacetoxyborohydride were added, followed by stirring for an hour. The reaction solution was diluted with chloroform, washed with an aqueous sodium hydroxide solution and a saturated aqueous sodium chloride solution successively, and the organic layer was dried over anhydrous magnesium sulfate. The solvent was evaporated under reduced pressure, and the resulting residue was purified by silica gel column chromatography (acetone:hexane:triethylamine=10:10:0.2) to give 0.70 g (yield: 48%) of 2'-O-acetyl-9-deoxo-9-hydroxy-9-O-[2-[N-methyl-N-(3-pyridylmethyl)amino]ethyl]erythromycin A.

(3) In 10 ml of methanol was dissolved 0.68 g (0.74 mmol) of the compound obtained in the above (2), followed by reflux under heating for 5 hours. The solvent was evaporated under reduced pressure to give 0.64 g (yield: 99%) of the title compound.

IonSprayMS: m/z=884.7 (M+H)$^+$ $^1$H-NMR (500 MHz, CDCl$_3$) δ(ppm): 0.91 (t, 3H, J=7.5 Hz, H-15), 2.17 (s, 3H, NCH$_3$), 2.29 (s, 6H, 3'-N(CH$_3$)$_2$), 4.57 (d, 1H, J=7.3 Hz, H-1'), 4.99 (d, 1H, J=3.5 Hz, H-1"), 5.11 (dd, 1H, J=9.5, 3.4 Hz, H-13)

$^{13}$C-NMR (125 MHz, CDCl$_3$) δ(ppm): 91.8 (C-9), 95.2 (C-1"), 102.2 (C-1'), 176.8 (C-1)

EXAMPLE 2

9-Deoxo-5-O-desosaminyl-9-hydroxy-9-O-[2-[N-methyl-N-(3-pyridylmethyl)amino]ethyl]-3-O-(2-pyridyl)acetylerythronolide A (1) In 1 N hydrochloric acid was dissolved 0.50 g (0.57 mmol) of the compound obtained in Example 1(3), followed by stirring for 2 hours. The reaction solution was neutralized with an aqueous sodium hydroxide solution and separated by addition of ethyl acetate. The organic layer was washed with a saturated aqueous sodium chloride solution and dried over anhydrous magnesium sulfate. The solvent was evaporated under reduced pressure, and purification of the residue by silica gel column chromatography gave 0.41 g of the decladinosyl compound quantitatively.

(2) In 5 ml of acetone was dissolved 0.40 g (0.61 mmol) of the compound obtained in the above (1), and then 0.1 ml (1.1 mmol) of acetic anhydride was added, followed by stirring overnight. After evaporation of the solvent under reduced pressure, the residue was dissolved in ethyl acetate and washed with a saturated aqueous sodium bicarbonate solution and a saturated aqueous sodium chloride solution successively, and the organic layer was dried over anhydrous magnesium sulfate. The solvent was evaporated under reduced pressure to give 0.41 g (yield: 91%) of the 2'-O-acetyl compound.

(3) In 3 ml of methylene chloride was dissolved 0.20 g (0.27 mmol) of the compound obtained in the above (2), and then 0.31 g (1.6 mmol) of 1-(3 -dimethylaminopropyl)-3-ethylcarbodiimide hydrochloride, 0.28 g (1.6 mmol) of 2-pyridylacetic acid hydrochloride and 0.066 g (0.54 mmol) of 4-dimethylaminopyridine were added, followed by stirring overnight. The reaction solution was diluted with chloroform and separated by addition of an aqueous sodium hydroxide solution. The organic layer was washed with a saturated aqueous sodium chloride solution and dried over anhydrous sodium sulfate. The solvent was evaporated under reduced pressure, and the resulting residue was dissolved in 30 ml of methanol and refluxed under heating for 3 hours. After evaporation of the solvent under reduced pressure, the resulting residue was purified by silica gel column chromatography (chloroform:methanol:aqueous ammonia=20:1:0.1) to give 0.11 g (yield: 48%) of the title compound.

FABMS (3-NBA): m/z=845 (M+H)$^+$ $^1$H-NMR (500 MHz, CDCl$_3$) δ(ppm): 0.85 (t, 3H, J=7.5 Hz, H-15), 2.20 (s, 3H, NCH$_3$), 2.29 (s, 6H, 3'-N(CH$_3$)$_2$), 4.15 (d, 1H, J=7.0 Hz, H-1'), 5.29–5.32 (m, 2H, H-3 and H-13)

$^{13}$C-NMR (125 MHz, CDCl$_3$) δ(ppm): 92.1 (C-9), 103.5 (C-1'), 170.2 (3-OCOR), 173.8 (C-1)

EXAMPLE 3

9-Deoxo-9-hydroxy-9-O-[2-[N-(4-quinolylmethyl)amino]ethyl]erythromycin A (1) In 100 ml of methanol was dissolved 5.1 g (6.2 mmol) of the compound obtained in Example 1(1), followed by reflux under heating for 5 hours. The solvent was evaporated under reduced pressure to give 4.8 g (yield: 48%) of 9-deoxo-9-hydroxy-9-O-(2-aminoethyl)erythromycin A.

(2) In 15 ml of methylene chloride was dissolved 2.0 g (2.6 mmol) of the compound obtained in the above (1), and then 0.44 g (2.8 mmol) of 4-quinolinecarboxyaldehyde and 1.1 g (5.2 mmol) of sodium triacetoxyborohydride were added, followed by stirring overnight. The reaction solution was diluted with chloroform, washed with water and a saturated aqueous sodium chloride solution successively, and dried over anhydrous magnesium sulfate. After evaporation of the solvent under reduced pressure, the resulting residue was purified by silica gel column chromatography (chloroform:methanol:aqueous ammonia=15:1:0.1) to give 1.9 g (yield: 80%) of the title compound.

IonSprayMS m/z=920.5 (M+H)$^+$ $^1$H-NMR (500 MHz, CDCl$_3$) δ(ppm): 0.90 (t, 3H, J=7.5 Hz, H-15), 2.29 (s, 6H, 3'-N (CH$_3$)$_2$), 4.53 (d, 1H, J=7.3 Hz, H-1'), 4.93 (d, 1H, J=4.6 Hz, H-1"), 5.03 (dd, 1H, J=9.5, 3.0 Hz, H-13)

$^{13}$C-NMR (125 MHz, CDCl$_3$) δ(ppm): 91.3 (C-9), 95.3 (C-1"), 102.3 (C-1'), 176.8 (C-1)

EXAMPLE 4

9-Deoxo-9-hydroxy-9-O-[2-[N-methyl-N-(4-quinolylmethyl)amino]ethyl]erythromycin A In 5 ml of methylene chloride was dissolved 0.50 g (0.54 mmol) of the compound obtained in Example 3(2), and then 0.1 ml (1.2 mmol) of 37% aqueous formaldehyde solution and 0.23 g (1.1 mmol) of sodium triacetoxyborohydride were added, followed by stirring 3 hours. The reaction solution was diluted with chloroform and washed with an aqueous sodium hydroxide solution and a saturated aqueous sodium chloride solution successively, and the organic layer was dried over anhydrous magnesium sulfate. The solvent was evaporated under reduced pressure, and the resulting residue was purified by silica gel column chromatography (chloroform:methanol:aqueous ammonia=15:1:0.1) to give 0.45 g (yield: 89%) of the title compound.

SIMS m/z=934 (M+H)$^+$ $^1$H-NMR (300 MHz, CDCl$_3$) δ(ppm): 0.93 (t, 3H, J=7.4 Hz, H-15), 2.29 (s, 6H, 3'-N(CH$_3$)$_2$), 2.30 (s, 3H, NCH$_3$), 4.57 (d, 1H, J=7.3 Hz, H-1'), 4.92 (d, 1H, J=4.3 Hz, H-1"), 5.07 (dd, 1H, J=9.0, 3.7 Hz, H-13), 7.54–7.61 (m, 2H, quinolyl), 7.70 (m, 1H, quinolyl), 8.11 (m, 1H, quinolyl), 8.17 (m, 1H, quinolyl), 8.93 (d, 1H, J=4.4 Hz, quinolyl)

EXAMPLE 5

9-Deoxo-5-O-desosaminyl-9-hydroxy-9-O-[2-[N-methyl-N-(3-quinolylmethyl)amino]ethyl]-3-O-(2-pyridyl)acetylerythronolide A Repeating the same procedures as in Example 2(1), (2) and (3) with 0.45 g (0.48 mmol) of the compound obtained in Example 4 gave 0.19 g (yield: 45%) of the title compound.

IonSprayMS m/z=895.5 (M+H)$^+$ $^1$H-NMR (500 MHz, CDCl$_3$) δ(ppm): 0.85 (t, 3H, J=7.5 Hz, H-15), 2.29 (s, 6H, 3'-N(CH$_3$)$_2$), 2.31 (s, 3H, NCH$_3$), 4.17 (d, 1H, J=7.3 Hz, H-1'), 5.26 (dd, 1H, J=11.0, 2.5 Hz, H-13), 5.36 (d, 1H, J=11.6 Hz, H-3)

$^{13}$C-NMR (125 MHz, CDCl$_3$) δ(ppm): 92.6 (C-9), 103.6 (C-1'), 170.3 (3-OCOR), 174.1 (C-1)

EXAMPLE 6

9-Deoxo-9-hydroxy-9-O-[2-(quinoline-8-sulfonylamino)ethyl]erythromycin A

In 5 ml of methylene chloride and 5 ml of pyridine was dissolved 0.52 g (0.67 mmol) of the compound obtained in Example 3(2), and then 0.69 g (3.0 mmol) of quinoline-8-sulfonylchloride was added, followed by stirring overnight. The reaction solution was diluted with chloroform and separated with an aqueous sodium hydroxide solution, and the organic layer was dried over anhydrous magnesium sulfate. The solvent was evaporated under reduced pressure, and the resulting residue was purified by silica gel column chromatography (chloroform:methanol:aqueous ammonia= 10:1:0.1) to give 0.57 g (yield: 92%) of the title compound.

IonSprayMS m/z=970.5 (M+H)$^+$ $^1$H-NMR (500 MHz, CDCl$_3$) δ(ppm) : 0.93 (t, 3H, J=7.5 Hz, H-15), 2.29 (s, 6H, 3'-N(CH$_3$)$_2$, 4.62 (d, 1H, J=7.3 Hz, H-1'), 4.89 (dd, 1H, J=11.0, 2.5 Hz, H-13), 5.04 (d, 1H, J=4.2 Hz, H-1"), 6.82 (t, 1H, J=4.3 Hz, NH)

$^{13}$C-NMR (125 MHz, CDCl$_3$) δ(ppm) : 93.1 (C-9), 94.9 (C-1"), 101.9 (C-1'), 177.0 (C-1)

EXAMPLE 7

9-Deoxo-9-hydroxy-5-O-desosaminyl-3-O-(2-pyridyl)acetyl-9-O-[2-(quinoline-8-sulfonylamino)-ethyl]erythronolide A Repeating the same procedures as in Example 2(1), (2) and (3) with 0.51 g (0.53 mmol) of the compound obtained in Example 6 gave 0.34 g (yield: 69%) of the title compound.

IonSprayMS m/z=931.5 (M+H)$^+$ $^1$H-NMR (500 MHz, CDCl$_3$) δ(ppm): 0.87 (t, 3H, J=7.3 Hz, H-15), 2.29 (s, 6H, 3'-N(CH$_3$)$_2$), 4.22 (d, 1H, J=7.3 Hz, H-1'), 5.07 (dd, 1H, J=10.4, 2.4 Hz, H-13), 5.35 (d, 1H, J=9.8 Hz, H-3), 6.91 (br, 1H, N-H)

$^{13}$C-NMR (125 MHz, CDCl$_3$) δ(ppm): 93.3 (C-9), 103.7 (C-1'), 170.6 (3-OCOR), 174.5 (C-1)

EXPERIMENT 1

The in vitro antibacterial activity of the compound obtained in Example 5, representative of the compounds according to the present invention, against various experimental bacteria was measured using sensitive disc media (produced by Eiken Chemical Co.) according to the MIC measuring method specified by the Japan Society of Chemotherapy. The results are expressed as MIC value (Minimum Inhibitory Concentration against microorganism, μg/ml), and shown in Table 1.

TABLE 1

| In Vitro Antibacterial Activity (μg/ml) | |
| --- | --- |
| Microorganism | Compound Example 5 |
| S. aureus 209-JC | 3.13 |
| S. aureus Smith | 6.25 |
| S. epidermidis IID866 | 3.13 |
| E. faecalis CSJ1212 | 1.56 |
| S. pneumoniae BM225 | 50 |
| S. pneumoniae BM205 | 100 |

INDUSTRIAL APPLICABILITY

The compounds of the present invention have an antibacterial activity not only against erythromycin-sensitive bacteria but also against erythromycin-resistant bacteria. Accordingly, the compounds of the present invention are useful as antibacterial agents for the treatment of bacterially infectious diseases in human beings and animals (including farm animals).

We claim:

1. An erythromycin A derivative represented by the formula:

wherein n is an integer of from 1 to 8, $R^1$ is a hydrogen atom or an alkyl group having 1 to 6 carbon atoms, $R^2$ is a pyridylmethyl group, a quinolylmethyl group, a pyridylsulfonyl group or quinolylsulfonyl group, $R^3$ is a hydrogen atom, an alkyl group having 1 to 6 carbon atoms or a cinnamyl group, $R^4$ is a cladinosyloxy group or a group represented by the formula:

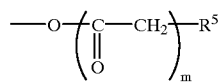

wherein m is 0 or 1, $R^5$ is a pyridyl group, a quinolyl group, a phenyl group, a phenyl group substituted with one, two or three members selected from the group consisting of alkyl groups having 1 to 6 carbon atoms, a nitro group, alkoxy groups having 1 to 3 carbon atoms and halogen atoms, or a pyridyl or quinolyl group substituted with one or two members selected from the group consisting of alkyl groups having 1 to 6 carbon atoms, a nitro group, alkoxy groups having 1 to 3 carbon atoms and halogen atoms; or a pharmaceutically acceptable salt thereof.

* * * * *